United States Patent
O'Connell (10) Patent No.: US 7,232,681 B2
(45) Date of Patent: Jun. 19, 2007

(54) PERSONAL CELL SAMPLING KIT

(76) Inventor: David O'Connell, 202 Waverly Way, Greensboro, NC (US) 27403-1622

( * ) Notice: Subject to any disclaimer, the term of this patent is extended or adjusted under 35 U.S.C. 154(b) by 614 days.

(21) Appl. No.: 10/421,939

(22) Filed: Apr. 24, 2003

(65) Prior Publication Data

US 2004/0214316 A1    Oct. 28, 2004

(51) Int. Cl.
*C12M 1/30* (2006.01)
(52) U.S. Cl. .............. 435/309.1; 435/307.1; 435/287.6; 435/810; 600/572
(58) Field of Classification Search ........... 435/287.6, 435/287.7, 288.1, 288.2, 307.1, 309.1, 306.1; 600/572
See application file for complete search history.

(56) References Cited

U.S. PATENT DOCUMENTS

| | | | | |
|---|---|---|---|---|
| 3,876,503 A * | 4/1975 | Mennen | ................ | 435/37 |
| 3,890,954 A * | 6/1975 | Greenspan | ................ | 600/572 |
| 3,954,564 A * | 5/1976 | Mennen | ................ | 600/572 |
| 4,311,792 A * | 1/1982 | Avery | ................ | 435/30 |
| 4,387,725 A * | 6/1983 | Mull | ................ | 600/572 |
| 4,582,787 A * | 4/1986 | Frankel | ................ | 435/5 |
| 4,770,853 A * | 9/1988 | Bernstein | ................ | 422/58 |
| 4,789,639 A * | 12/1988 | Fleming | ................ | 436/178 |
| 6,197,574 B1 * | 3/2001 | Miyamoto et al. | ........ | 435/287.6 |
| 2002/0197738 A1 * | 12/2002 | Matsumoto et al. | ........ | 436/518 |

FOREIGN PATENT DOCUMENTS

JP    07308184 A  * 11/1995

* cited by examiner

*Primary Examiner*—William H. Beisner
(74) *Attorney, Agent, or Firm*—Whitham Curtis Christofferson & Cook, PC (57) ABSTRACT

A kit for obtaining and shipping personal cell samples is provided. The kit contains such items as a transport tube, and collection swabs for obtaining a cell sample. The tube has a media plug impregnated with dehydrated media positioned within the tube near the top of a region of restricted diameter, and a compartment of rehydrating fluid located in a cap on the tube. Upon crushing the cap, the rehydrating fluid is released and rehydrates the media plug. When the collection swab is inserted into the transport tube, the swab pushes the rehydrated media plug through the region of restricted diameter and into the bottom of the tube. The collection surface of the swab thus maintains contact with the rehydrated media plug.

16 Claims, 5 Drawing Sheets

PERSONAL CELL SAMPLING KIT

BACKGROUND OF THE INVENTION

1. Field of the Invention

The invention generally relates to a kit for cell sampling for personal use. In particular, the invention provides a kit for obtaining and shipping personal cell samples.

2. Background of the Invention

In the wake of spectacular advances in molecular and cell biology, which include such feats as the completion of the first sequencing of a human genome, much interest has been generated in applying the acquired knowledge to the treatment of disease conditions. Examples of potential applications include the use of gene therapy to cure diseases, and the use of cells to grow replacement tissue or organs. In particular, the capability now exists to determine the precise sequence of an individual's DNA, opening the possibility of the development of "tailor made" DNA- and/or cell-based therapies for an individual. Such individualized procedures could eliminate certain risk factors such as the rejection of cells or cellular components originating from a non-self donor. Unfortunately, therapies of this type are by and large still in the early stages of development and it may well be many years before they are readily accessible.

Many conditions which may eventually be amenable to treatment in this manner are associated with or develop with advancing age. Further, it is well known that genetic material itself ages and undergoes changes during an individual's lifetime. Thus, in general, cells harvested from an aging individual are less robust than those from the same individual at an earlier age. This observation has prompted the creation of facilities designed for the long-term storage of cells. In particular, cells can be harvested from an individual relatively early in life in the expectation that, as technology advances or as the need arises, the cells can be revived for use in the same individual for a gene- or cell-based therapy. In order to make such a possibility available to large segments of the population, it is necessary to have facile, inexpensive methods for harvesting suitable cells. It is particularly useful to have techniques available that can be carried out by the individuals themselves without any specialized training, and that provide a viable, sterile sample of suitable cells for preservation.

One such method is provided by the previously known Personal Gene Sampling (PGS) cell harvesting kit. The kit, which is available by mail, provides a sterile work surface (a small medical drape) sterile collection swabs, and sterile sample transport tubes for receiving the swabs after a sample has been obtained, as well as a transport bag for containing the transport tubes for shipment to a cryo-preservation facility. A sample-collection surface is located at one end of the collection swab and is formed by positioning suitable absorbent material at that end of the swab. The cell source (e.g. the inside of the cheek) is contacted directly with sample-collecting surface of the swab, for example, by wiping the surface across the cell source. Cells from the source adhere to the sample-collection surface and are removed and transported (for example, by mail) to a cryo-facility.

The sample transport tubes have the feature of containing a plug of material saturated is with media and movably positioned near the top of the tube. Upon insertion of a collection swab into the tube, the sample-collection end of the swab contacts the saturated plug and causes the plug to move further down into the tube. The plug is fitted in the tube and will slide into the tube only as far as it is pushed by the swab. Therefore, upon completion of insertion of the swab, contact is maintained between the collection end of the swab and the saturated plug, thus exposing the cells on the collection surface to the media in the plug. The media previously suggested for use in the kit is Lebovitz's 15 (L-15) media, supplemented with antibiotic and antimycotic reagents.

However, locating the saturated media plug near the mouth of the transport tube provides a ready route of contamination as soon as the tube is opened for use. Further, the use of a media saturated plug means that the shelf-life of the kit is only as long as that of the liquid media. Liquid media is well-known to be readily prone to contamination, and to decomposition during storage.

The prior art has thus far failed to provide a personal cell-sampling kit that overcomes these disadvantages.

SUMMARY OF THE INVENTION

It is an object of this invention to provide a kit for cell sampling for personal use by an individual. The kit includes: at least one collection swab that is sterile and comprises at least one collection surface for collecting a cell sample and at least one tube for receiving the collection swab. The tube contains dehydrated media positioned on a support material that is positioned within the tube so as to make direct contact with the collection surface of the collection swab when the collection swab is received within the tube. The tube also contains rehydrating liquid in a compartment on the tube. The dehydrated media may be lyophilized together with the support material. The support material may be, for example, hypoallergenic surgical sponge or general-use sponge. The dehydrated media may comprise, for example, 95% L-15 media; 5% fetal bovine serum; and at least one antimicrobial agent such as an antibiotic or an antifungizone.

The present invention further provides a kit for cell sampling which includes at least one collection swab which is sterile and comprises at least one collection surface for collecting a cell sample, and at least one tube for receiving the collection swab. The tube contains support is material positioned within the tube so as to make direct contact with the collection surface of the collection swab when the collection swab is inserted into the tube. The tube also includes media in a compartment on the tube. The media is dissolved or dispersed in a fluid carrier for transport of the media onto the support material. The support material may be hypoallergenic surgical sponge or general-use sponge. The media may comprises 95% L-15 media; 5% fetal bovine serum; and at least one antimicrobial agent such as an antibiotic or an antifungizone.

The present invention further provides a method of making a kit for cell sampling. The method comprises the steps of: providing a collection swab with at least one collection surface for collecting a cell sample; forming a tube for receiving the collection swab, wherein the tube includes a compartment containing rehydrating fluid (e.g. water); lyophilizing together media and a support material; positioning the support material within the tube so that direct contact is made between a collection surface of the collection swab and the support material when the collection swab is received within said tube; and packaging the tube and the collection swab to form a kit for cell sampling. All components of the kit may be sterile.

DETAILED DESCRIPTION OF THE PREFERRED EMBODIMENTS OF THE INVENTION

The present invention provides a cell sampling kit for personal use. The kit provides a means for non-professional individuals to obtain and make ready for transport a personal cell sample. The cell sample may then shipped to a facility for further processing by professionals, for example, for culturing and/or clonal expansion of the cells, cryopreservation, DNA typing analysis, genetic manipulations, and the like. However, the step of obtaining a cell sample is made convenient by the kit of the present invention. The need for the individual to travel to a processing facility or to solicit the services of a professional for obtaining the sample is eliminated.

The kit of the present invention provides advantages in both the form and composition of the media that is utilized, and in the design of the cell collection and transport devices. The media is provided in a dehydrated form in the kit, and is reconstituted by the user just prior to collecting the cell sample. The provision of dehydrated medium is advantageous in that the kits of the present invention have an exceptionally long shelf life. This is advantageous from a manufacturing and storage point of view, and from the point of view of the consumer. The elements of the kit which contain the media can be manufactured, packaged into kits and stockpiled if need be, or shipped to distributors or customers with confidence that the kit will function as intended for a long period of time with little or no risk of media contamination or decomposition. For example, the shelf life of a kit of the present invention is in the range of about 1 to about 3 years. In addition, the media is supplied in dehyrated form on a media plug that is initially positioned approximately half-way down the transport tube. Thus, the risk of contamination upon opening the tube is minimized. Yet the media plug is still pushed through the restriction in the transport tube to the bottom of the tube by the collection area tip of the swab, thereby insuring that full contact and saturation is made between the media saturated plug and the cells on the collection area.

Figure 1A:
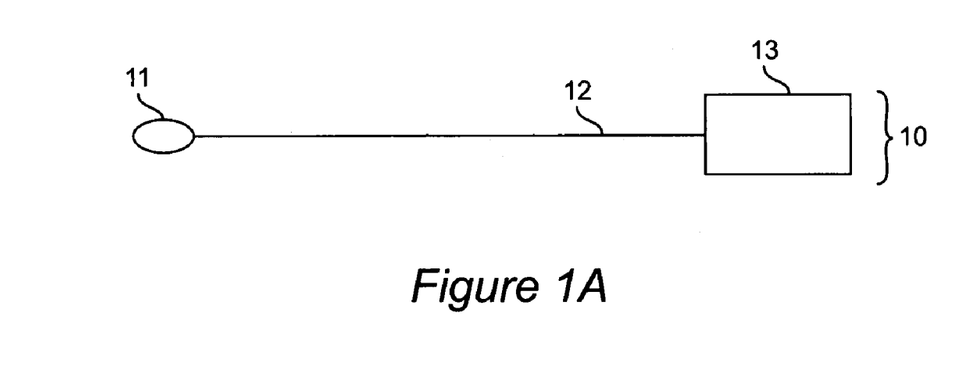
FIGS. 1A–B. Schematics of the swab component of the kit.
Figure 1B:
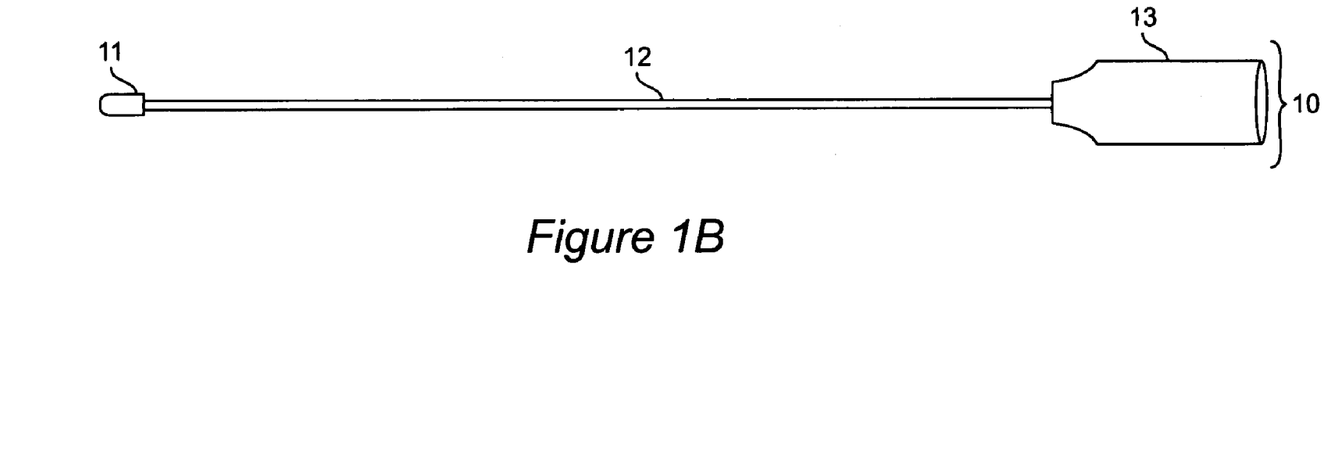
Figure 2A:
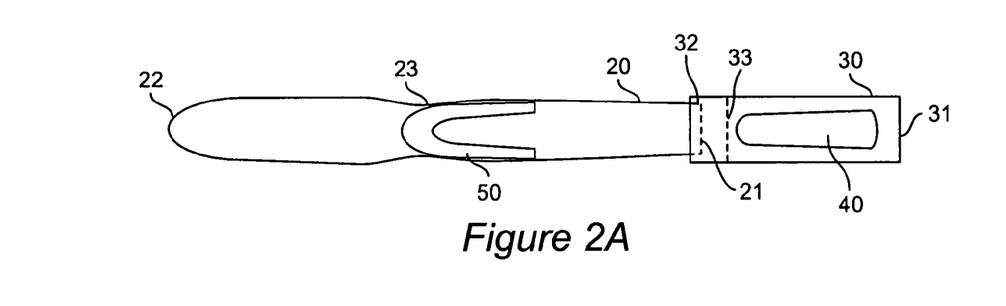
FIGS. 2A–C. Schematics of the transport tube. A, with a cap that covers the end of the transport tube; B, with a cap that inserts into the transport tube; C, area of restricted diameter is present but outside walls of the tube remain parallel.

Some components of the kit of the present invention may be understood in reference to FIG. 1. FIGS. 1A and B show alternative embodiments of a swab 10 comprised of a handle 12, a collection area 11 attached to one end of the handle 12, and a closure cap 13 affixed to the opposite end of the handle 12. In a preferred embodiment of the invention, two sterile swabs 10 are provided in "blister-pack" protective packaging in the kit. Also provided in a blister pack protective packaging are two transport tubes of the type shown in FIGS. 2A and B. FIGS. 2A and B show alternative embodiments of transport tube 20 having an open top end 21, a closed bottom end 22, and restricted diameter region 23, located between open top end 21 and closed bottom end 22. Restricted diameter region 23 represents a portion of the tube at which the interior diameter of the transport tube is narrower than the diameter elsewhere within the transport tube 20, i.e. above or below the restricted diameter region 23. The transport tube 20 also contains support material ("media plug") 50. Prior to placement of the cell sample in the transport tube, media plug 50 is located above or partially within restricted diameter region 23 of the transport tube 20. Media plug 50 is permeated with dehydrated media.

Figure 2B:
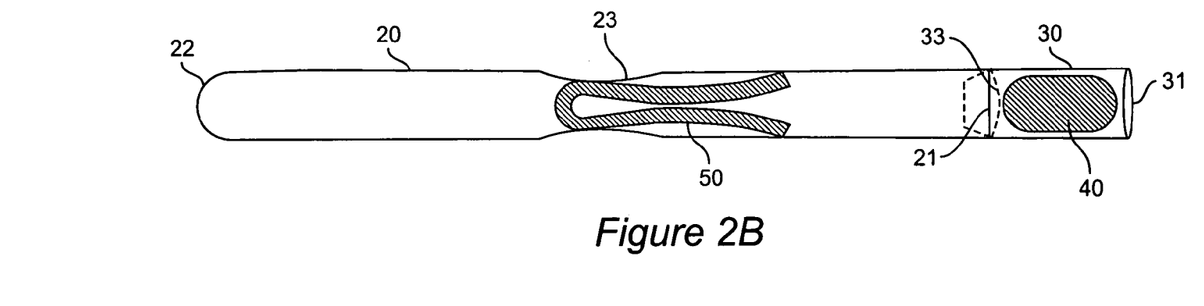
Figure 3A:
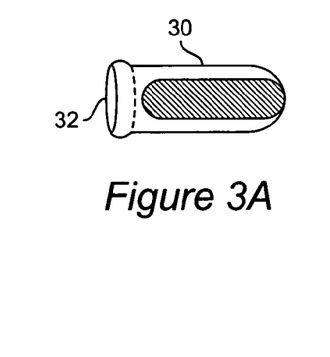
FIGS. 3A–E. Schematics of: A, a cap that covers the end of the transport tube with enclosed ampule; B, a cap that inserts into the transport tube with enclosed ampule; C, tilted side view of cap with perforated surface; D and E, end view of perforated surface.
Figure 3B:
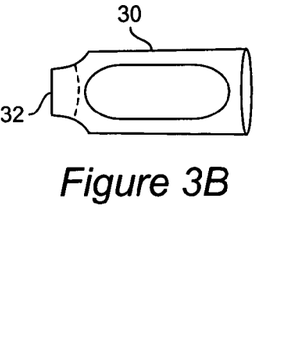
Figure 3C:
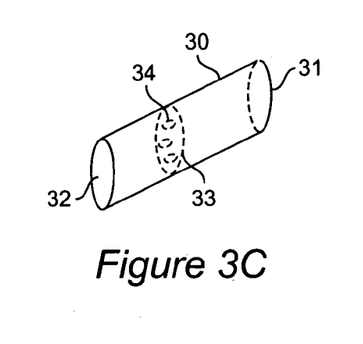
Figure 3D:
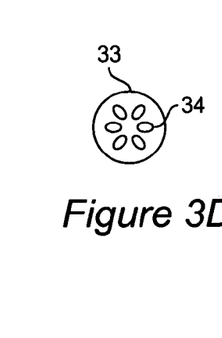
Figure 3E:
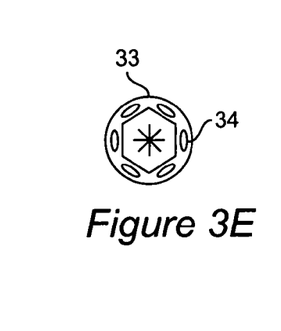

Prior to use of the kit, cap 30 is detachably engaged with open top end 21 of the transport tube 20. Cap 30 comprises a closed top end 31, an open bottom end 32, and a perforated surface 33 disposed within the cap 30, the circumference of which is parallel to that of closed top end 31 and open bottom end 32. In differing embodiments, the open bottom end 32 of the cap surrounds the open top end 21 of the tube (FIGS. 2A and 3A) and in others, the open bottom end 32 of the cap is inserted into the open top end 21 of the tube (FIGS. 2B and 3B). The cap 30 houses a container for rehydrating liquid 40. The perforated surface 33 is located within the cap 30 below the container for rehydrating liquid 40. FIG. 3C shows a tilted side view of the cap 30 with perforated surface 33 with perforations 34, and FIGS. 3D and E show end views of alternative embodiments of the perforated surface 33 with perforations 34.

Just prior to collecting a cell sample, the user "crushes" the cap 30 to rupture the container for rehydrating liquid 40, and the rehydrating liquid flows out of the cap 30, through the perforated surface 33, and into the transport tube 20. The rehydrating liquid wets the media plug 50 and the dehydrated media on the media plug becomes hydrated. The process of hydrating the dehydrated media constitutes "activation"of the transport tube.

Figure 4A:
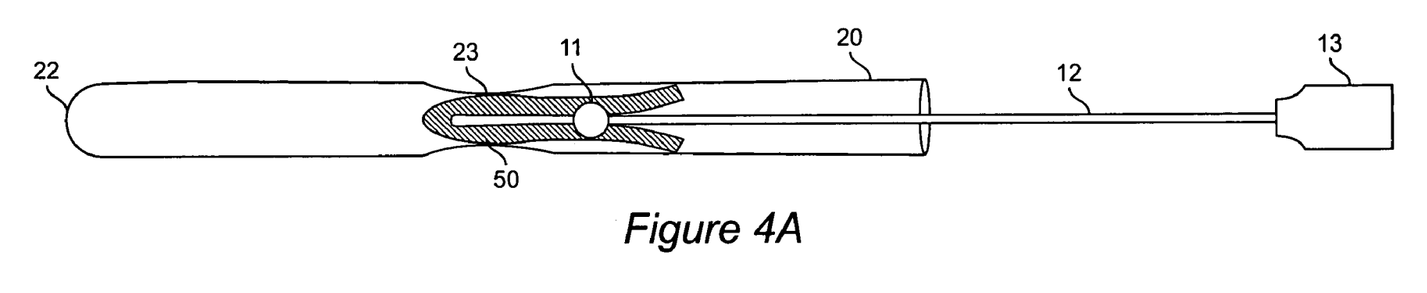
FIGS. 4A and B. A, insertion of used collection swab into the transport tube. B, used collection swab fully inserted into the transport tube and closure cap in place.
Figure 4B:
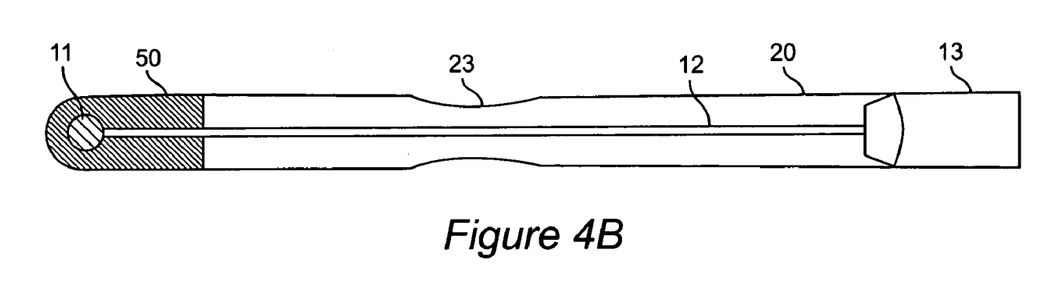

After activation of the transport tube, the cap 30 is removed and may be discarded. A cell sample is collected on the collection area 11 of the swab 10 (details are given in the Examples section), and the swab is then inserted into the transport tube, collection area 11 first (see FIG. 4A). The collection area 11 tip of the swab is placed against the rehydrated media plug 50 and the media plug 50 is pushed through restricted diameter region 23 of the transport tube and into the bottom closed end 22 of the tube. The collection area 11 of the swab is thus enclosed by the media plug (see FIG. 4B), and the cells on the collection area 11 exposed to media during transport to the processing facility.

With respect to the design and composition of the various kit components, the transport tube 20 may be made from any of a variety of suitable materials which are well known to those of skill in the art. The transport tube should be made of material that is rigid enough to withstand shipping and cell sampling procedures. Examples of materials suitable for making the transport tube include but are not limited to various "plastics", natural and synthetic polymers, and non-breakable polypropylene. Further, the dimensions/volume of the transport tube will be in the range of about approximately five to seven inches, and preferably about six inches in length; and in the range of about one-quarter (¼) to about three-quarters (¾) of an inch in diameter, and preferably about seven sixteenths (⁷⁄₁₆) of an inch in diameter.

Likewise, the cap 30 should also be made of durable material and should be robust enough to withstand shipment, but the cap 30 must also be flexible enough to allow manual deformation of the cap in order to crush the container of rehydrating liquid that is located inside the cap. Examples of materials suitable for making the cap include but are not limited to various "plastics", natural and synthetic polymers, and the like which are well-known to those of skill in the art.

The dimensions of the cap will be in the range of about from one half (½) to one and one-half (1½) inches in length, and preferably approximately one and one quarter (1¼) of an inch in length. Those of skill in the art will recognize that the diameter at the end of the cap that the swabs are connected to is slightly smaller (or larger) than the outside diameter of the open end of the transport tube so as to provide a secure snap closure when forced over (or into) the open end of the transport tube assembly. Further, while the cap is constructed to fit tightly onto or into the transport tube, it is not an airtight fit. Rather, the closure is such that the free exchange of gas between the internal volume of the capped swab transport tube assembly and the external environment is allowed. The feature decreases the chance of the cap "popping" off during travel in, for example, an unpressurized aircargo compartment or the like.

In addition, those of skill in the art will recognize that the transport tube and cap may be of various colors and display various designs for either practical or aesthetic reasons. For example, the bottom closed end of the sample tube may be rounded, flat, etc., and the exterior surface of the transport tube and cap may be smooth or ribbed; may have one or more flat surfaces to prevent rolling of the transport tube; or bear designs such as logos, patterns that are purely decorative, etc. All such variations are intended to be covered by the scope of the present invention.

The detachable, disposable cap 30 contains within it a container for storage of the rehydrating fluid. Many variations of such a container exist. For example, the container may be an "ampule" style container with rigid walls that crack upon the application of pressure. Examples include but are not limited to a typical glass ampule. Such an ampule may be housed within a compartment in the cap. Alternatively, the container may be a "sack" which bursts and releases its contents upon the application of pressure. Examples include but are not limited to sack-like containers of, for example, flexible plastic "sheet" material such as polycarbonate, polyvinyl chloride (PVC), polyethylene or polypropylene plastics. Alternatively, the container may be a compartment within the cap that is an integral part of the cap. In this case, the compartment would possess at least one surface that is predisposed to rupture upon the application of pressure to the walls of the cap. Such a surface would be located directly above the perforated surface 33 of the cap so that upon rupture of the surface, the rehydrating liquid would flow through the perforated surface and into the transport tube. Those of skill in the art will recognize that many styles of container exist which may be utilized in the practice of the present invention. Any such container may be utilized so long as the container can reliably retain the rehydrating fluid until its release is desired, and then release the rehydrating fluid upon the application of manual pressure. In general, the container will have a volume in the range of about 0.4 ml to about 0.5 ml and preferably from about 0.49 ml to about 0.51 ml.

The detachable cap 30 is attached to collection tube 20 so that it remains attached during shipment and handling, but can be detached in a facile manner by the end-user after activation of the transport tube. For example, the diameter of the cap may be slightly larger than the opening of the tube so that the open end of the tube can be inserted at least partially into the cap, e.g. the cap can "snap" onto the tube. Alternatively, the cap may be a double action security cap that slides (e.g. by means of a "ridge ring") over the neck of the swab tube and tightly grips the inside (by means of a restricted interior diameter) and outside of the tube. Further, the junction between the cap and tube may be sealed with a strip of removable material such as tamper seal tape or a large pre-attached identification label. Alternatively, the diameter of the cap may be slightly smaller than the opening of the tube so that the open end of the cap can be inserted at least partially into the transport tube and be retained by "snapping" into the tube; and the junction between the cap and tube may be sealed with a strip of removable material such as tamper seal tape or a large pre-attached identification label. Alternatively, the cap 30 may be molded as part of collection tube 20 with perforations at the junction between the cap 30 and the tube 20, such that the perforations may be broken and the cap released by "twisting" the cap 30 relative to the collection tube 20. Or, the cap may simply screw onto or into the tube. The exact means of attaching the cap 30 to collection tube 20 are not a key feature of the invention and many designs may be utilized, so long as the cap 30 is securely retained on the collection tube 20 until use so that the contents of the collection tube 20 remains sterile, and yet can be removed without difficulty after activation of the transport tube.

Figure 5A:
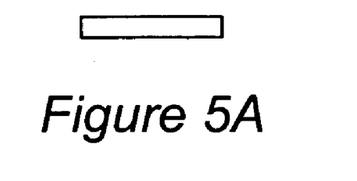
FIGS. 5A–I. A–E, various embodiments (side views) of the perforated surface; F–G, top (F) and side (G) views of a media plug; H–I, side (H) and top (I) views of a media plug preformed to fit the shape of the tube.
Figure 5B:
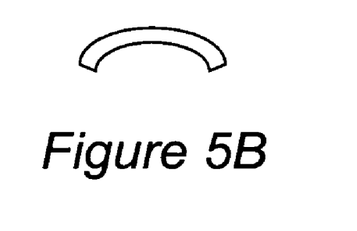
Figure 5C:
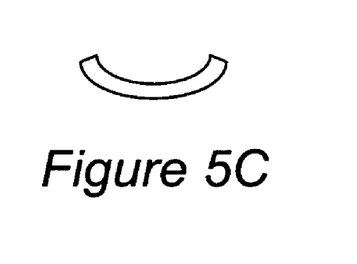
Figure 5D:
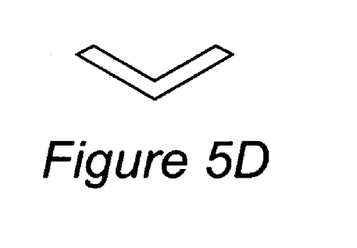
Figure 5E:
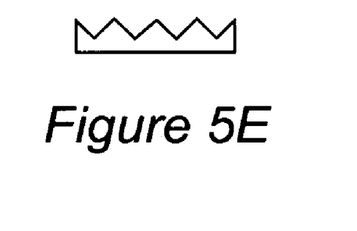

The cap 30 also contains a perforated surface 33, the circumference of which is generally parallel to that of closed top end 31 and open bottom end 32 of the cap. The perforated surface 33 is located below the container for rehydrating liquid 40 and between closed top end 31 and open bottom end 32 of the cap 30. The perforated surface serves to retain the container for rehydrating liquid 40 in the upper portion of the cap, but the perforations through the perforated surface allow the rehydrating liquid to flow out of the cap when the container for rehydrating liquid 40 is broken during activation of the transport tube. Those of skill in the art will recognize that many designs of such a perforated surface are possible. For example, the perforated surface may be essentially planar (FIG. 5A), or it may be concave or convex (FIGS. 5B and C), or somewhat "funnel-shaped" with a depression in the center (FIG. 5D), or with multiple depressions (FIG. 5E). Further, the perforated surface may be manufactured separately and inserted into the cap, or may be integrally molded in the cap. In general, the perforated surface may be manufactured of materials similar to those used for manufacture of the transport tube. The perforated surface may be of any practical thickness, and the perforations may be of any practical size and shape, so long as the container for rehydrating liquid is retained above the perforated surface, and the rehydrating liquid can pass through the perforations upon release from the container.

Figure 2C:
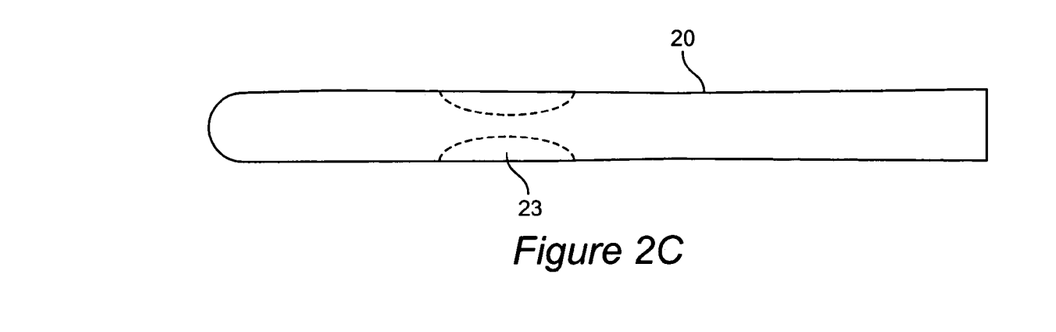

The purpose of introducing a restricted diameter region 23 into the tube is to provide a point of resistance for positioning a media plug within the transport (collection) tube. The media plug 50 is positioned within the collection tube 20 so that the media plug 50 abuts the edge of restricted diameter region 23 or is partially inserted into the top end of restricted diameter region 23. In this manner, free or accidental movement of media plug 50 further into the bottom of collection tube 20 is impeded by the narrow diameter of restricted diameter region 23. However, restricted diameter region 23 does not completely close off the tube; when the swab is introduced into the tube, pressure exerted on the media plug 50 by the end of the swab will force the media plug 50 through restricted diameter region 23 and into the bottom end 22 of the tube. In addition, the restriction in the transport tube forces the saturation/dispensing of the medium from the media plug onto the swab tip by a "squeezing effect" that results from being pushed down and through the restriction. This action insures that the swab becomes wetted with media. The diameter of restricted diameter region 23 must thus be large enough to readily accommodate the swab plus the media plug 21. The exact dimensions of the restricted diameter region 23 are not a key feature of the invention, and may be of any suitable size, so long as the media plug can be retained prior to insertion of the swab, and pushed through the restricted diameter region 23 and into the bottom of the transport tube upon the application of gentle pressure from the swab. In general, the diameter of the restricted diameter region 23 will be in the range of about three sixteenths (3/19) to about six sixteenths (6/16) of an inch, and preferably in the range of about four sixteenths (4/16) to about five sixteenths (5/16) of an inch. Restricted diameter region 23 will include less than about ½% of the total length of the transport tube, or no more than about one half (½) to three quarters (¾) of an inch, and preferably about 5/16 of an inch of the total length of the transport tube. The area at the bottom of the transport tube (i.e. below the restricted diameter region 23) should be large enough to snugly accommodate the media plug with rehydrated media and the collection surface end of the swab. Further, the outer walls of the transport tube may or may not be narrowed in restricted diameter region 23. For example, in FIGS. 2A and B, the entire wall of the tube is recessed to form restricted diameter region 23. However, as depicted in FIG. 2C, the outer walls of the tube may remain parallel along the entire length of the tube and restricted diameter region 23 may be defined by a narrowing of the inner walls.

Figure 5F:
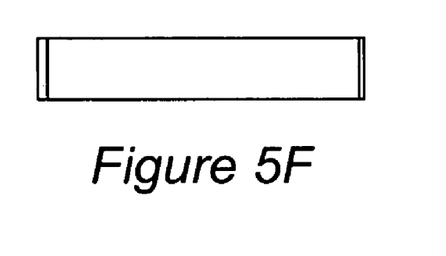
Figure 5G:
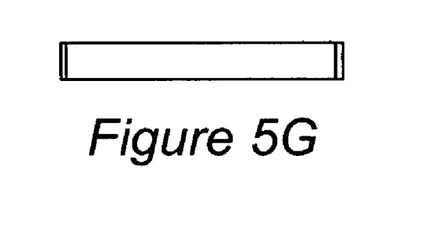
Figure 5H:
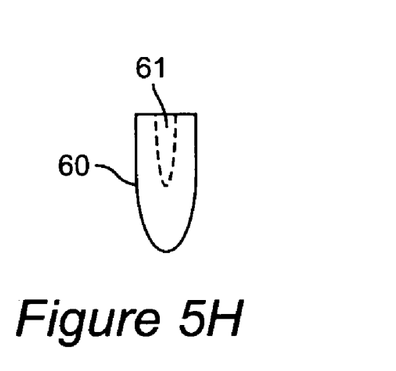
Figure 5I:
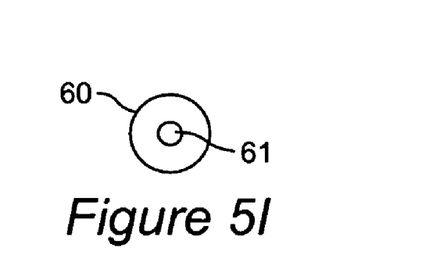

The media plug 21 is impregnated with dehydrated media, and may be of any of any suitable shape and composition. For example, the media plug may be a flat "strip" or "disc-shaped" piece of material of a size and shape that is suitable for facile insertion into the transport tube. FIGS. 5F and G show a top and side view, respectively, of a rectangular media plug. In this case, the area of the media plug will be in the range of about 4 to about 5 cm$^2$, and preferably about 4.5 to about 4.7 cm$^2$ and of a thickness of about 0.1 to about 1 cm and preferably about 0.3 to about 0.5 cm. Alternatively, the media plug may be preshaped, for example with an interior recess to receive the collection area end of the swab, and an exterior surface that conforms to the shape of the tube. 5H and I show a side and a top view, respectively, of a preshaped media plug in which 60 denotes the exterior surface of the plug and 61 denotes the interior recess. The total absorptive area of such a preshaped plug will be in the range of about 15 cm$^2$ to about 20 cm$^2$ and preferably about 17.5 cm$^2$ to about 18 cm$^2$. Those of skill in the art will recognize that many materials exist which would be suitable for use as a media plug in the present invention. Examples include but are not limited to various hypoallergenic, sterile fabrics also known as surgical or general-use sponge, and the like. In general, the material should be capable of absorbing a sufficient quantity of media to support the collected cells upon rehydration, capable of being sterilized, and resistant to deterioration during the dehydration process. The material must also be flexible enough to be moved through the restricted diameter region 23 and into the bottom of the tube by the action of the swab stick.

Approximately about 500 μL to about 1 mL, and preferably about seven hundred twenty five (725) μL to about seven hundred and fifty (750) μL of media is dehydrated on the media plug. The process of dehydrating the media on the media plug may be carried out prior to insertion of the media plug into the tube. Alternatively, the media plug may be impregnated with media and then inserted, or inserted and then impregnated, and the dehydration may be carried out with the media plug already in the tube. Those of skill in the art will recognize that several means exist to dehydrate media, including but not limited to lyophilization (i.e. "freeze-drying"), evaporation of liquid components under vacuum, by accelerating the evaporation process by exposure of the media to a stream of gas (air, $N_2$, argon, etc.), by heating, and the like. Further, a combination of these methods may be used. In a preferred embodiment, the method for dehydrating the media used in the kits of the present invention is lyophilization.

The media composition that is utilized in the cell collecting device of the present invention is one that is suitable for maintaining buccal cell samples. In a preferred embodiment, the media comprises 95% Leibovitz's L-15 and 5% fetal bovine serum, volume to volume. The media may further contain antimicrobial agents such as antibiotics (e.g. penicillin, streptomycin, etc.) and antimycotic agents (e.g. fungizone, etc.) Typically, such antimicrobial agents will be present in the amount of about 100 units per mL (penicillin), 50 micrograms per mL (streptomycin) and 2 micrograms per mL (fungizone). However, those of skill in the art will recognize that the concentrations of such antimicrobial agents may vary by about ±10% in the media without significantly altering effectiveness. In addition, the media may contain various other additives which are well-known to those of skill in the art, such as amino acids, salts, buffering agents, or sugars, and the like, in order to make the media more compatible with the buccal cell samples, or to facilitate the freeze-drying or subsequent rehydration of the media.

The kit of the present invention includes rehydrating fluid. The rehydrating fluid is an aqueous-based fluid comprised of sterile high-quality water (for example, distilled, deionized, or otherwise purified water). In general, the composition of the rehydrating solution will be in the range of about 95 to about 100% $H_2O$, and preferably in the range of about 99 to about 100% $H_2O$. In addition, the rehydrating fluid may contain various salts, buffering agents, wetting agents, and the like. Those of skill in the art will recognize that such additives must be compatible with maintaining the viability of the cell sample that will be shipped in the reconstituted media. The quantity of rehydrating fluid in the container in the range of about 0.25 mL to about 1 mL, and preferably about 0.49 ml to about 0.51 ml.

In the practice of the present invention, the term "swab" is used in the general sense of collection material attached to one end or "tip" of an elongated "stick-like" handle. With respect to the present invention, the collection swab is sterile as provided to the user, the elongated portion is of sufficient length so that the collection material on one end can be suitably placed within the tube, and the collection material has at least one surface that is suitable for use in collecting the cell sample. Those of skill in the art will recognize that many types of materials exist for making swabs which would be appropriate for use in the practice of the present invention. For example, the elongated handle potion may be made from wood, various types of plastic, polypropylenes, and or natural and synthetic polymers and the like. The handle must be rigid enough to withstand the sampling process and insertion into the tube, able to reliably retain the collection material, stable to the serialization process, and non-toxic to the cell sample. With respect to the attached collection material which provides at least one surface for collecting a cell sample, many materials are available which are suitable for forming such a collection surface. The material must be such that it exhibits some resistance to the bodily surface from which the cell sample will be detached, i.e. the material must be capable of dislodging cells from, for example, the interior of the mouth, e.g. inside the cheek, when the bodily surface is contacted with the material. Further, the material should be amenable to sterilization, and non-toxic to the cell sample. Examples of suitable materials include but are not limited to cotton, various natural and synthetic fibers or "cloth"—like materials, various porous "foam" type plastic materials, (e.g. polyurethane foam) and/or other polymers. In a preferred embodiment, the material is rayon sponge material.

The particular shape and size of the collection area in general, and the cell collection surface(s) in particular, are not key features of the invention, and many shapes and sizes which would be suitable for use in the present invention are known to those of skill in the art. For example, the collection area may be "tear-shaped", spherical, hemispherical, cylindrical, rectangular, etc.; and may be symmetrical or "flattened" in appearance. Further, the surface may be more or less smooth, or may be rough, containing ridges or grooves. Any shape may be utilized for the collection material portion of the swab, so long as adequate numbers of cells adhere to and are retained on the collection material for transfer to the transport tube. The collection surface itself may constitute the entire surface of the collection material, or may constitute a portion of the material, e.g. one side of a "flattened" shape of collection material.

In addition, the swab 10 contains a closure cap 13. The closure cap maybe attached to the handle-end of the collection swab so that, rather than grasping the handle end of the collections swab throughout the operations of collecting the cell sample and placing the used collection swab within the transport tube, the user grasps the closure cap itself. In this embodiment, placement of the collection swabs within the transport tube coincides with placement of the closure cap onto or into the open end of the transport tube. Attachment of the swab shaft to the closure cap eliminates one extra step for the consumer (e.g. attaching the swab to the cap for a secure fit into the transport tube, or placing the swab within the tube and then attaching the closure cap to the tube). However, those of skill in the art will recognize that the present invention may also be practiced by using a closure cap to which the used collection swab is attached by the user prior to insertion into the transport tube, or by using a collection swab that is entirely separate from and never joined to the closure tube. In a preferred embodiment, the collection swab is attached to the closure cap. In this embodiment, the length of the collection area 11 plus handle 12 plus closure cap 13 is such that upon placement of the closure cap and attached swab within the transport tube 20, the closure cap 13 will "snap", "lock", screw, or otherwise engage the cap into place with the open end 31 of the transport tube 20, thus sealing the tube. Concomitantly, the collection surface of the swab will be seated at an appropriate position near the bottom of the transport tube. Those of skill in the art will recognize that many cap designs and mechanisms of attaching a cap onto or within a tube exist which may be utilized in the kit of the present invention. For example, many potential variations in the size and shape of the cap, and the material from which it is made, are possible. Further, many attachment mechanisms are known to those of skill in the art. Any such mechanism may be utilized, so long as the closure cap is firmly attached to the tube and reliably seals the transport tube for shipping.

Several cell sample types may practically and safely be obtained by a lay individual using the kit of the present invention. Examples include but are not limited to buccal cells, dermis cells, mesodermal cells, epithelium cells, mucous cells, etc. In a preferred embodiment of the invention the cells that are sampled are buccal cells, which are located within the mouth on the inside of the cheek. In the Examples section of the application, the collection of buccal cells is illustrated in detail.

The kit of the present invention may further contain other components. For example, tamper seal labels, used to reseal the tops of the sample transport tubes, are included, as is a Sample Delivery Pouch which the end-user of the kit will use to return the cell sample(s) to the processing facility. In addition, the kit may contain detailed instructions for using the kit, and various legal agreements, warranties, disclaimers, and the like.

While the kit of the present invention is described as intended for obtaining a "personal" cell sample, those of skill in the art will recognize that an individual may also wish to preserve cells from individuals other than him- or herself. For example, parents may wish to obtain cell samples from their children. A reservoir of such cells would, for example, be useful as a definitive identification tool, or for future medical applications such as organ regenration. Alternatively, an individual may wish to obtain a cell sample from a domesticate animal, for example, in order to later develop a clone of the animal, or to provide a definitive means of identification, for example, for purposes of breeding. In yet another application, the kit provides a facile means for obtaining cell samples from a population, for example from those convicts required to give a DNA sample, or from subjects in a medical study.

One example of a potential use of present invention is to collect and preserve cells from the mouth against the event of damage to the eye such as to the cornea. Tens of thousands of people each year suffer damage, either from disease or accident, to the front part of their eyes, the cornea. This can only be repaired by grafting on new corneal tissue taken from someone else. Many hospitals and clinics store eye tissue for this purpose. But people who have had this treatment have to take powerful and sometimes unpleasant drugs to stop the body's immune system from rejecting the graft. Even so, the rejection often occurs. Scientists have recently reported success in developing a new way to repair damaged eyes using stem cells taken from the mouth. Doctors have developed an approach that involves growing a new segment of cornea using stem cells taken from the patient's mouth. Because the cells come from the patient's own body, no immunosuppressive drugs are needed to prevent rejection. The treatment is currently in human trials in which eight out of nine patients monitored regained their vision as a result of the procedure.

EXAMPLES

Example 1

Obtaining a Personal Cell Sample for Cryopreservation

An individual obtains the kit of the present invention by mail. The following steps for using the kit to obtain a personal cell sample are outlined in detail in the instructions that are provided in the kit.

Step 1. The instructions provided with the kit note that cell samples should be obtained in the morning before brushing the teeth. Several hours of refraining from food and drink insures a higher quality of collected cells. The user should prepare and clean a suitable work surface. On the work surface, the user lays out one sample transport tube blister pack and one sterile swabs stick blister pack.

Step 2. The user partially removes one of the two swab sticks from the sterile swab stick blister pack, taking care to leave the tip (collection area) portion of the swab well inside the protection of the blister pack, touching only the handle or cap portions of the swab.

Step 3. The user removes one of the two transport tubes from the sterile blister pack and takes note of the position of the container for rehydrating liquid within the detachable cap of the transporter tube. With the transporter tube held in an upright position, (i.e. with the detachable cap at the top), and with the detachable cap still attached to the transporter tube, the user "crushes" the top of the detachable cap with his/her fingers, thereby breaking the container for rehydrating liquid and releasing the rehydrating liquid from the container. The rehydrating liquid flows down the cap, through the perforations of the perforated surface, into the transport tube, and onto the media plug. The dehydrated media on the media plug is thereby rehydrated by the rehydrating liquid. The transport tube may be tapped or shaken lightly to aid in the flow of rehydrating liquid toward the tube. The transport tube has now been "activated".

Step 4. The other transport tube is removed from the blister pack and set aside on the work surface to be used as a support for a swab stick.

Step 6. The "used" swab stick is then removed from the mouth and placed on the work surface using the transport tube as a support. The swab should be placed so that the collection tip is in the air and does not come into contact with any other object. The user then removes the detachable cap from the previously activated (i.e. media rehydrated) transport tube.

Step 7. The used swab stick is held in one hand and the activated transport tube (sans cap) is held in the other. The collection area of the used swab stick is aligned with the open end of the transport tube and the swab stick is inserted into the transport tube. During insertion of the swab stick, the collection area of the swab stick will encounter the media plug, which now contains rehydrated media. The user continues to apply pressure to the swab stick to push the media plug through the restricted diameter region of the transport tube until the media plug is resting on the bottom closed end of the transport tube. The length of the swab stick and attached closure cap is such that when the collection area tip of the swab stick is inserted far enough to firmly seat the media plug against the bottom closed end of the transport tube, the closure cap will be positioned to encounter the open end of the transport tube. The closure cap is designed to snap or lock into place with the open end of the transport tube an thereby seal the transport tube. The collection area "tip" of the swab stick remains in contact with the media plug. In this manner, the cells located on the collection surface are contacted by freshly rehydrated medium, and the transport tube is securely closed.

Step 5. The user completely removes one swab stick from the blister pack, taking care not to allow contact between the collection area of the swab stick and any other surface. The collection area end of the swab stick is then placed inside the user's mouth and held firmly against the inside of the cheek. The user then slowly wipes the collection area portion of the swab across the inside of the cheek at least five times on one cheek and then at least five times on the inside surface of the other cheek.

Step 8. The procedure is repeated with the remaining swab stick and transport tube.

Step 9. The user writes his/her name on a tamper seal that is provided with the kit. The user places a completed tamper seal across the junction of the transport tube and the closure cap. The closed and sealed transport tubes are placed in a sample delivery pouch (also provided with the kit) and shipped back to the processing facility. Shipment should be carried out as soon as possible. The cell sample should arrive at the processing facility within at most 48 hours of collection, and preferably within 24 hours. Instructions included in the kit may also note that the closed and sealed transport tubes should not be frozen. Rather, they should be stored at room temperature until shipment.

Example 2

Processing of Cells

Ultimately, the cells will be cryopreserved at the processing facility. Prior to freezing, the cells are removed from the collection surface of the collection swab and placed in culture.

Several methods of removing the cells are known to those of skill in the art, including removing the collection surface from the swab and placing it in liquid culture medium, clipping off the end of the swab that contains the collection surface and placing it in liquid culture medium, streaking the collection surface across an agar plate to dislodge cells from the collection surface, agitating liquid media with the collection surface of the swab to dislodge cells, and the like. Cells are grown in suitable liquid media under conditions which are optimized for the particular cell type, and which are well-known to those of skill in the art. The details of an exemplary protocol are given below.

Alternatively, for some purposes (e.g. for nuclear transfer procedures) it may be advisable to simply remove the cells from the collection surface and freeze them directly withour culturing, or even to freeze the cells on the collection surface.

Typically liquid $N_2$ is used to preserve tissue culture cells, either in the liquid phase (−196° C.) or in the vapor phase (−156° C.). Freezing can be lethal to cells due to the effects of damage by ice crystals, alterations in the concentration of electrolytes, dehydration, and changes in pH. To minimize the effects of freezing, several precautions are taken. First, a cryoprotective agent which lowers the freezing point, such as glycerol or DMSO, is added. The freezing medium typically use is 90% serum, 10% DMSO. Also the cells are slowly cooled from room temperature to −80° C. to allow the water to move out of the cells before it freezes. The optimal rate of cooling is 1°–3° C. per minute. This is accomplished by using either a freezing chamber to regulate the freezing at the optimal rate by periodically pulsing in liquid nitrogen, or a low tech device called a "Mr. Frosty". The Mr. Frosty is filled with 200 ml of isopropanol at room temperature and the freezing vials containing the cells are placed in the container and the container is placed in the −80° C. freezer. The effect of the isopropanol is to allow the tubes to come to the temperature of the freezer slowly, at about 1° C. per minute. Once the container has reached −80° C. (about 4 hours or, more conveniently, overnight) the vials are removed from the Mr. Frosty and immediately placed in the liquid nitrogen storage tank. Cells are stored at liquid nitrogen temperatures because the growth of ice crystals is retarded below −130° C."The following is an exemplary protocol for the cryopreservation of cells. The protocol is provided for the purposes of example only and is not intended to be limiting.

1. Cells to be frozen must not be infected with microorganisms (bacteria, yeast, mold, mycoplasma and in special cases virus). Therefore, testing of the cell culture for these potential contaminants is carried out prior to freezing. In addition the cells must be viable and in the exponential phase of growth.
2. Gently harvest the cells. Spin down the cells as gently as possible (should not exceed 400× g). Resuspend the cells in growth medium at room temperature to a concentration of about $2 \times 10^6$ to $2 \times 10^7$ cells per ml. Count the viable cells.
3. To avoid damage to the cell during freezing, a cryoprotectant is added to the growth medium in which the cells are to be frozen. Glycerol or DMSO (dimethyl sulphoxide) in 10% concentrations is most commonly used. Glycerol is non-toxic to the cells (and to the personnel) and can be added directly to the cells. DMSO enters the cells more rapidly than glycerol. DMSO is toxic to the cells (and to the personnel) if high concentrations are used and if the cells are exposed to DMSO for prolonged periods (e.g. 10% DMSO for several hours at room temperature). Because heat is generated when DMSO is dissolved in aqueous solutions, it cannot be added directly to the cells. DMSO must be diluted to e.g. 20% in medium, allowed to cool to below 37° C. and subsequently added to the cells to a final concentration of 10%.
4. Mix cells and cryoprotectant at room temperature to final concentration of viable cells in the range between $10^6$ and $10^7$ cells per ml and final concentration of cryoprotectant of 10%. Cells frozen in lower or higher cell concentration often tend to have less viability. Allow the cryoprotectant to enter the cells. At least 20 minutes and, for DMSO, not more than 30 minutes should pass before the cooling procedure is started. This is usually the time it takes to aliquot the cells into CryoTube™ Vials.
5. If a uniform batch of cells where every aliquot is representative of the whole batch is required, all the cells must be collected at this step into one vial and properly mixed, before aliquoting is performed. Usually 1 ml aliquots are used, but other volumes can also be used. As 1 ml cryo vials are very small, it is advisable to use sterile gloves when opening and closing the vials in order to minimize the risk of contamination during aliquoting. Care should be taken not to exceed the maximum filling volume of the CryoTube vial. CryoTube vials made of polypropylene are most commonly used for storage of cells. When cells are to be stored in the vapour phase of liquid nitrogen or in a −140° C. mechanical freezer, CryoTube vials with internal thread and silicone gasket are the safest to use. This kind of cryo vial has the best seal and, provided that the vial is properly closed (neither too loose nor too tight), there is no risk of contamination with microorganisms during storage.
6. The most common cooling rate used is 1° C. per minute in the range from room temperature and down to below −50° C. Once the temperature is below −50° C., the CryoTube vials can be submerged directly in liquid nitrogen (−196° C.). Special equipment for precise controlling of the cooling rates is available on the market. Such equipment is very expensive and usually only needed for very sensitive cells. In most cases the cooling rate can be controlled in a less expensive manner: As a rule of thumb, a −70° C. mechanical freezer cools a litre cube of water 1° C./minute.
7. In theory, cells can be stored indefinitely below −130° C., as no biological process takes place below this temperature. Cells stored for prolonged periods above −130° C. tend to be less stable.

Example 3

Retrieval and Use of Cryogenically Preserved Cells at a Later Time

The purpose of storage at low temperature is to keep and maintain materials for later use, e.g. to preserve original cells for later culture. The viability of the cells after cryopreservation depends on their ability to cope with the variety of stresses imposed on them during the freezing and thawing procedures. Most mammalian cells can be stored at temperatures below −130° C. for many years. For example, it is not unusual for cells to be retrieved after 25 or more years after cryopreservation.

An increasing number of medical therapies require viable, specialized cells recovered from cryogenic storage. For example, medical applications of embryonic stem cells will probably require cells that are genetically matched to the patient, so as to avoid rejection. Nuclear transfer, the central technology of cloning, could in principle provide matched cells if the donor cells are cryopreserved cells, because a cloned embryo derived from a patient's cell sample could yield embryonic stem cells. As individuals become more apprised of the need to store a cellular sample for medical treatments, the need for a convenient, and economic zoetic cell collection/transportation device and method such as provided by the invention will become of greater demand. The cells collected and transported (as a potential source for therapeutic stem cells or other medical applications) therefore need to be usable for culturing, nuclear transfer or fusion cloning after shipment.

Once an individual desires to obtain the cryopreserved cells, several options will be available for retrieval of the cells upon request. For example, frozen cells may be directly shipped on dry ice to a hospital at which a medical procedure is being performed, or to a laboratory at which the cells will be manipulated for use in a medical procedure. Alternatively, the cells may be thawed, placed in culture, and then transported to the requested facility of choice. In the latter case, care must be taken to ensure that the cells are thawed under conditions favorable to the cell's survival and ability to grow and divide. An exemplary protocol is provided below, and is intended to be illustrative and non-limiting.

Protocol for Thawing of Cells:
1. To obtain the best possible survival of the cells, thawing of the cells must be performed as quickly as possible. Once the CryoTube vial is removed from the freezer/liquid nitrogen tank, it should be placed directly into a 37° C. water bath and shaken until it is completely thawed. If liquid nitrogen has entered the CryoTube vial, it will explode upon warming, because liquid nitrogen will expand 700 times during the warming process. Personnel should always wear protective clothes, glasses and gloves, while handling CryoTube vials from liquid nitrogen tanks, and should transport the vial in a covered, insulated bucket or box. An explosion may happen seconds after the vial has been removed from the liquid nitrogen.
2. To avoid transfer of microorganisms from the freezer/liquid nitrogen tank or the water bath to the laminar flow cabinet and subsequently to the culture, the CryoTube vials are soaked in 70% ethanol before they are transferred to the laminar flow cabinet.
3. If the cryo protectant used is glycerol, the cells can be diluted 10 times directly into a TC fl ask or TC dish. If DMSO is used, the cells should be washed once in growth medium before being added to the TC flask in fresh growth medium. Some cells are very sensitive at this stage of the procedure, and it may be advisable to dilute the DMSO stepwise to minimize the osmotic stress imposed upon the cells when DMSO is diluted. It is advisable to take out a sample of the thawed cells for a viability test before the cells are placed in the incubator.
4. In order to avoid physical damage of cells that form a monolayer, such cultures should be left untouched in the incubator for at least 16 hours before assessing the result.

After thawing and reculturing of the cells in a suitable media, they may be shipped to their destination by any of several techniques which are well-known to those of skill in the art. For example, they may be placed in sealed tubes of media, or placed on a temporary support medium for shipment. A shipping device similar to that of the present invention may also be utilized, except that the cells are collected onto the collection surface of the swab by exposure of the collection surface to the newly established culture, rather than to an original source of cells.

While the invention has been described in terms of its preferred embodiments, those skilled in the art will recognize that the invention can be practiced with modification within the spirit and scope of the appended claims. Accordingly, the present invention should not be limited to the embodiments as described above, but should further include all modifications and equivalents thereof within the spirit and scope of the description provided herein.

I claim:

1. A kit for cell sampling, comprising,
   at least one collection swab, wherein said collection swab is sterile and comprises at least one collection surface for collecting a cell sample,
   at least one tube for receiving said collection swab, said tube containing dehydrated media positioned on a support material, wherein said support material is positioned within said tube at a narrow diameter region spaced away from a closed bottom end of said tube so as to make direct contact with said at least one collection surface of said collection swab when said collection swab is received within said tube, said support material being moveable from said narrow diameter region towards said closed bottom end of said tube under a force applied by said collection swab whereby said support material is squeezed while being pushed down and through said narrow diameter region; and,
   rehydrating liquid in a compartment within a cap that is removably secured on an open end of said tube.

2. The kit of claim 1, wherein said dehydrated media is lyophilized together with said support material.

3. The kit of claim 1, wherein said support material is selected from the group consisting of hypoallergenic surgical sponge or general-use sponge.

4. The kit of claim 1, wherein said dehydrated media comprises
   95% L-15 media;
   5% fetal bovine serum; and
   at least one antimicrobial agent.

5. The kit of claim 4, wherein said at least one antimicrobial agent is an antibiotic.

6. The kit of claim 4, wherein said at least one antimicrobial agent is an antifungizone.

7. The kit of claim 1 wherein said support material is shaped with a recess in a top surface which receives an end of said collection swab.

8. A kit for cell sampling, comprising,
   at least one collection swab, wherein said collection swab is sterile and comprises at least one collection surface for collecting a cell sample,
   at least one tube for receiving said collection swab, said tube containing support material, wherein said support material is positioned within said tube at a narrow diameter region spaced away from a closed bottom end of said tube so as to make direct contact with said at least one collection surface of said collection swab when said collection swab is received within said tube, said support material being moveable from said narrow diameter region towards said closed bottom end of said tube under a force applied by said collection swab whereby said support material is squeezed while being pushed down and through said narrow diameter region; and,
   media in a compartment within a cap that is removably secured on an open end of said tube, said media being dissolved or dispersed in a fluid carrier for transporting said media onto said support material.

9. The kit of claim 8, wherein said support material is selected from the group consisting of hypoallergenic surgical sponge or general-use sponge.

10. The kit of claim 8, wherein said media comprises
    95% L-15 media;
    5% fetal bovine serum; and
    at least one antimicrobial agent.

11. The kit of claim 10, wherein said at least one antimicrobial agent is an antibiotic.

12. The kit of claim 10, wherein said at least one antimicrobial agent is an antifungizone.

13. The kit of claim 8 wherein said support material is shaped with a recess in a top surface which receives an end of said collection swab.

14. A method of making a kit for cell sampling comprising the steps of
    providing a collection swab comprising at least one collection surface for collecting a cell sample,
    providing a tube for receiving said collection swab, wherein said tube comprises a compartment within a cap that is removably secured on an open end of said tube, wherein said compartment contains rehydrating fluid, and wherein said tube includes a narrow diameter region spaced away from a closed bottom end of said tube, lyophilizing together media and a support material, positioning said support material within said tube at said narrow diameter region so that direct contact is made between a collection surface of said collection swab and said support material when said collection swab is received within said tube and so that said support material is moveable from said narrow diameter region towards said bottom of said tube under a force applied by said collection swab whereby said support material is squeezed while being pushed down and through said narrow diameter region, packaging said tube and said collection swab to form a kit for cell sampling.

15. The method of claim 14, wherein all components of said kit are sterile.

16. The method of claim 14 further comprising the step of forming said support material to be haped with a recess in a top surface which receives an end of said collection swab.

* * * * *